United States Patent
Kontiola et al.

(10) Patent No.: US 11,471,050 B2
(45) Date of Patent: Oct. 18, 2022

(54) METHOD AND ARRANGEMENT FOR EYE PRESSURE MEASUREMENTS

(71) Applicant: Photono Oy, Helsinki (FI)

(72) Inventors: Antti Kontiola, Helsinki (FI); Edward Hæggström, Helsinki (FI); Ari Salmi, Helsinki (FI); Heikki Nieminen, Helsinki (FI)

(73) Assignee: PHOTONO OY, Helsinki (FI)

( * ) Notice: Subject to any disclaimer, the term of this patent is extended or adjusted under 35 U.S.C. 154(b) by 79 days.

(21) Appl. No.: 15/257,429

(22) Filed: Sep. 6, 2016

(65) Prior Publication Data

US 2016/0374554 A1 Dec. 29, 2016

Related U.S. Application Data

(63) Continuation of application No. PCT/FI2015/050133, filed on Mar. 3, 2015.

(30) Foreign Application Priority Data

Mar. 4, 2014 (FI) ...................................... 20145205

(51) Int. Cl.
*A61B 3/16* (2006.01)
*A61B 5/00* (2006.01)
(Continued)

(52) U.S. Cl.
CPC ............ *A61B 3/165* (2013.01); *A61B 5/0051* (2013.01); *A61B 8/10* (2013.01); *A61B 3/102* (2013.01)

(58) Field of Classification Search
CPC .......... A61B 3/165; A61B 5/0051; A61B 8/10
See application file for complete search history.

(56) References Cited

U.S. PATENT DOCUMENTS 3,948,248 A * 4/1976 Zuckerman ............ A61B 3/165
600/457
5,251,627 A 10/1993 Morris
(Continued)

FOREIGN PATENT DOCUMENTS

CN 1229345 A 9/1999
CN 101083934 A 12/2007
(Continued)

OTHER PUBLICATIONS

Zhu, et al., The contribution of accommodation and the ocular surface to the microfluctuations of wavefront aberrations of the eye, 2006, Ophthal. Physiol. Opt., 26, p. 439-446. (Year: 2006).*
(Continued)

*Primary Examiner* — Daniel L Cerioni
*Assistant Examiner* — Raymond P Dulman
(74) *Attorney, Agent, or Firm* — Nixon & Vanderhye

(57) ABSTRACT

An intraocular pressure measurement arrangement is disclosed for measuring pressure of an eye of a patient. The arrangement can include at least one source for producing mechanical waves of several frequencies from a distance to the eye of the patient to generate at least one surface wave to the eye, a detector for detecting at least one surface wave from a distance from the eye to extract surface wave information, and a device for determining pressure information of the eye based on the surface wave information.

4 Claims, 3 Drawing Sheets

(51) Int. Cl.
   *A61B 8/10*   (2006.01)
   *A61B 3/10*   (2006.01)

(56) References Cited

U.S. PATENT DOCUMENTS

| | | | |
|---|---|---|---|
| 5,830,139 A | 11/1998 | Abreu | |
| 5,865,742 A | 2/1999 | Massie | |
| 6,030,343 A | 2/2000 | Chechersky et al. | |
| 6,694,173 B1* | 2/2004 | Bende | A61B 5/0095 600/407 |
| 6,976,959 B2* | 12/2005 | Fresco | A61B 3/16 600/398 |
| 8,998,810 B2 | 4/2015 | Kontiola | |
| 2002/0097374 A1* | 7/2002 | Payne | A61B 5/0059 351/200 |
| 2003/0078486 A1 | 4/2003 | Klein et al. | |
| 2004/0193033 A1 | 9/2004 | Badehi et al. | |
| 2008/0103381 A1 | 5/2008 | Kontiola | |
| 2008/0242965 A1 | 10/2008 | Norris et al. | |
| 2009/0306493 A1 | 12/2009 | Kontiola | |
| 2010/0069737 A1* | 3/2010 | Jinde | A61B 3/165 600/399 |
| 2010/0249569 A1 | 9/2010 | Jinde et al. | |
| 2010/0324406 A1 | 12/2010 | Miwa | |
| 2011/0118609 A1* | 5/2011 | Goldshleger | A61F 9/00834 600/476 |
| 2011/0208060 A1* | 8/2011 | Haase | A61B 5/021 600/453 |
| 2012/0150013 A1 | 6/2012 | Peyman | |
| 2012/0277569 A1 | 11/2012 | Hogan | |
| 2013/0085370 A1 | 4/2013 | Friedman et al. | |
| 2014/0163329 A1* | 6/2014 | Brown, Jr. | G06K 9/00892 600/301 |
| 2016/0066786 A1 | 3/2016 | Kontiola | |
| 2016/0374555 A1 | 12/2016 | Kontiola et al. | |

FOREIGN PATENT DOCUMENTS

| | | |
|---|---|---|
| CN | 101190122 A | 6/2008 |
| DE | 19512711 C1 | 12/1996 |
| EP | 2236075 A1 | 10/2010 |
| FI | 20135401 A | 10/2014 |
| GB | 938222 A | 10/1963 |
| WO | WO 2014/170556 A1 | 10/2014 |

OTHER PUBLICATIONS

Wang, et al., A focused air-pulse system for optical-coherence-tomography-based measurements of tissue elasticity, 2013, Laser Physics Letters, 10, p. 1-6 (Year: 2013).*

Li, et al., Noncontact all-optical measurement of corneal elasticity, May 15, 2012, Optics Letters, vol. 37, p. 1625-1627 (Year: 2012).*

Orssengo, et al., Determination of the True Intraocular Pressure and Modulus of Elasticity of the Human Cornea in vivo, 1999, Bulletin of Mathematical Biology, 61, p. 551-572 (Year: 1999).*

Zhu, et al., The contribution of accommodation and the ocular surface to the microfluctuations of wavefront aberrations of the eye, 2006, Ophtal. Physiol. Opt., 26, p. 439-446 (Year: 2006).*

Nair, et al., Heartbeat optical coherence elastography: corneal biomechanics in vivo, Feb. 2021, Journal of Biomedical Optics, vol. 26, p. 020502-1-020502-8 (Year: 2021).*

International Search Report (PCT/ISA/210) dated Jun. 11, 2016, by the European Patent Office as the International Searching Authority for International Application No. PCT/FI2015/050133.

Written Opinion (PCT/ISA/237) dated Jun. 11, 2016, by the Japanese Patent Office as the International Searching Authority for International Application No. PCT/FI2015/050133.

Search Report dated Oct. 29, 2014, by the Finnish Patent Office in corresponding Finnish Patent Application No. 20145205.

International Preliminary Report on Patentability (PCT/IPEA/409) dated May 25, 2016, by the Swedish Patent Office as the International Preliminary Examining Authority for International Application No. PCT/FI2015/050133.

Alam, S. K. et al., 'Detection of intraocular pressure change in the eye using sonoelastic Doppler ultrasound'. Ultrasound in Medicine and Biology, vol. 20, No. 8, 1994, p. 751-758, ISSN 0301-5629, DOI: 10.1016/0301-5629(94)90032-9, XP 023258908. (9 pages).

Ionophone, Wikipedia article [online], May 29, 2013 (May 29, 2013). Retrieved from the Internet: <URL: http://en.wikipedia.org/w/index.php?title=Ionophone&oldid=557426731>. [Retrieved on Oct. 14, 2014.].

Plasma speaker, Wikipedia article [online], Feb. 22, 2014 (Feb. 22, 2014). Retrieved from the Internet: <URL: http://en.wikipedia.org/w/index.php?title=Plasma_speaker&oldid=596617125>. [Retrieved on Oct. 14, 2014.] (4 pages).

Tanter, M. et al., 'High-Resolution Quantitative Imaging of Cornea Elasticity Using Supersonic Shear Imaging'. IEEE Transactions on Medical Imaging, vol. 28, No. 12, Nov. 25, 2009, p. 1881-1893, ISSN 0278-0062, DOI 10.1109/TMI.2009.2021471, XP011281241. (14 pages).

Zhang, X.-Y. et al., 'Preliminary Study on the Effect of Stiffness on Lamb Wave Propagation in Bovine Corneas', Proceedings of the 35th Annual Internation Conference of the IEEE EMBS, Osaka, Japan, Jul. 3-7, 2013. Piscataway, NJ: IEEE, 2013, ISSN 1557-170X, DOI: 10.1109/EMBC.2013.6609702, p. 1120-1123, XP 032488337. (5 pages).

Office Action dated May 28, 2018, by the Chinese Patent Office in corresponding Chinese Patent Application No. 201610875022.1. (12 pages).

O.V. Rudenko et al., "Theoretical Foundations of Nonlinear Acoustics", Translated from Russian by Robert T. Beyer, Published by Consultants Bureau, a division of Plenum Publishing Corporation, New York, 1977 (p. 1).

Office Action (Notification of the First Office Action) dated Oct. 25, 2017, by the Chinese Patent Office in corresponding Chinese Patent Application No. 201580011876.9, and an English Translation of the Office Action. (23 pages).

Office Action (Notification of Reasons for Refusal) dated Nov. 20, 2018, by the Japanese Patent Office in corresponding Japanese Patent Application No. 2016-197655, and an English Translation of the Office Action. (6 pages).

Office Action dated Jan. 19, 2018, by the Finnish Patent Office in corresponding Finnish Patent Application No. 20145205. (8 pages).

Communication pursuant to Article 94(3) EPC issued in European Patent Application No. 15 710 219.5-1126 dated Mar. 5, 2021.

* cited by examiner

METHOD AND ARRANGEMENT FOR EYE PRESSURE MEASUREMENTS

RELATED APPLICATION

This application claims priority as a continuation application under 35 U.S.C. § 120 to PCT/FI2015/050133, which was filed as an International Application on Mar. 3, 2015 designating the U.S., and which claims priority to Finnish Application 20145205 filed in Finland on Mar. 4, 2014. The entire contents of these applications are hereby incorporated by reference in their entireties.

FIELD

Intraocular pressure (IOP) plays a major role in the pathogenesis of open angle glaucoma, a leading cause of blindness. There are about 150 million people with glaucoma globally, about half of which are unknowingly affected and without diagnosis. The prevalence of glaucoma increases with aging of the human population and it is expected that this will increase by 30% the number of glaucoma cases during the next decade. The only way to currently treat glaucoma is by lowering the intraocular pressure (IOP).

An IOP measurement is the most practical way of screening open angle glaucoma. However, screening large parts of the population is needed to find undiagnosed cases.

The other type of glaucoma is the narrow angle glaucoma that causes a sudden IOP increase that may cause blindness in a few days. Since one per mile of the population is affected with acute narrow angle closure glaucoma, it is mandatory to diagnose acute glaucoma by measuring IOP in community emergency departments of general medicine. Consequently it would be beneficial if every doctor's of would have the ability to measure IOP.

BACKGROUND INFORMATION

Contact methods (e.g. Goldmann tonometry, Mackay-Marg tonometry) for measuring IOP mostly use an anesthetic to carry out the measurement and are thus impractical to, for example, screen large human populations.

U.S. Patent Application Publication No. 2010/0249569 A1 presents a non-contact ultrasonic tonometer for IOP measurements, which employs piezo-electric transducers to excite wave signals into the eye. The positions of the transducers have to be exactly measured, which makes the IOP measurement procedure complex and slow. Also temperature variations cause error and uncertainty in the IOP measurement information together with possible errors in position measurements. The shape of the eye also introduces bias (=error) into the measurement.

U.S. Pat. No. 6,030,343 presents a method that is based on an airborne ultrasonic beam that is reflected from the cornea—the same beam measures and actuates the eye. The actuation is done by a narrow band ultrasonic tone burst, which deforms the cornea, and the system measures the phase shift from the deformed eye.

Known solutions do not achieve a convenient and low-cost device for measuring IOP precisely and comfortably for the patient by non-contact measurements.

SUMMARY

An intraocular pressure measurement arrangement is disclosed for measuring pressure of an eye of a patient, wherein the arrangement comprises: at least one source for producing an acoustic or a mechanical wave from a distance coupling to an eye of a patient to produce surface waves of several frequencies by utilizing at least one of a patient heartbeat and breathing; means for detecting at least one surface wave from a distance from an eye to extract surface wave information; and means for determining pressure information of an eye based on said surface wave information.

An intraocular pressure measurement method is also disclosed for measuring pressure of an eye of a patient, wherein the method comprises: producing an acoustic or a mechanical wave from a distance coupling to the eye of the patient to produce surface waves of several frequencies by utilizing at least one of a patient heartbeat and breathing; detecting at least one surface wave from a distance from the eye to extract surface wave information; and determining pressure information of the eye based on said surface wave information.

BRIEF DESCRIPTION OF THE DRAWINGS

Other features and advantages of the present disclosure will become apparent to those skilled in the art upon reading the detailed description of the embodiments in conjunction with the accompanying drawings, wherein.

DETAILED DESCRIPTION

Figure 1:
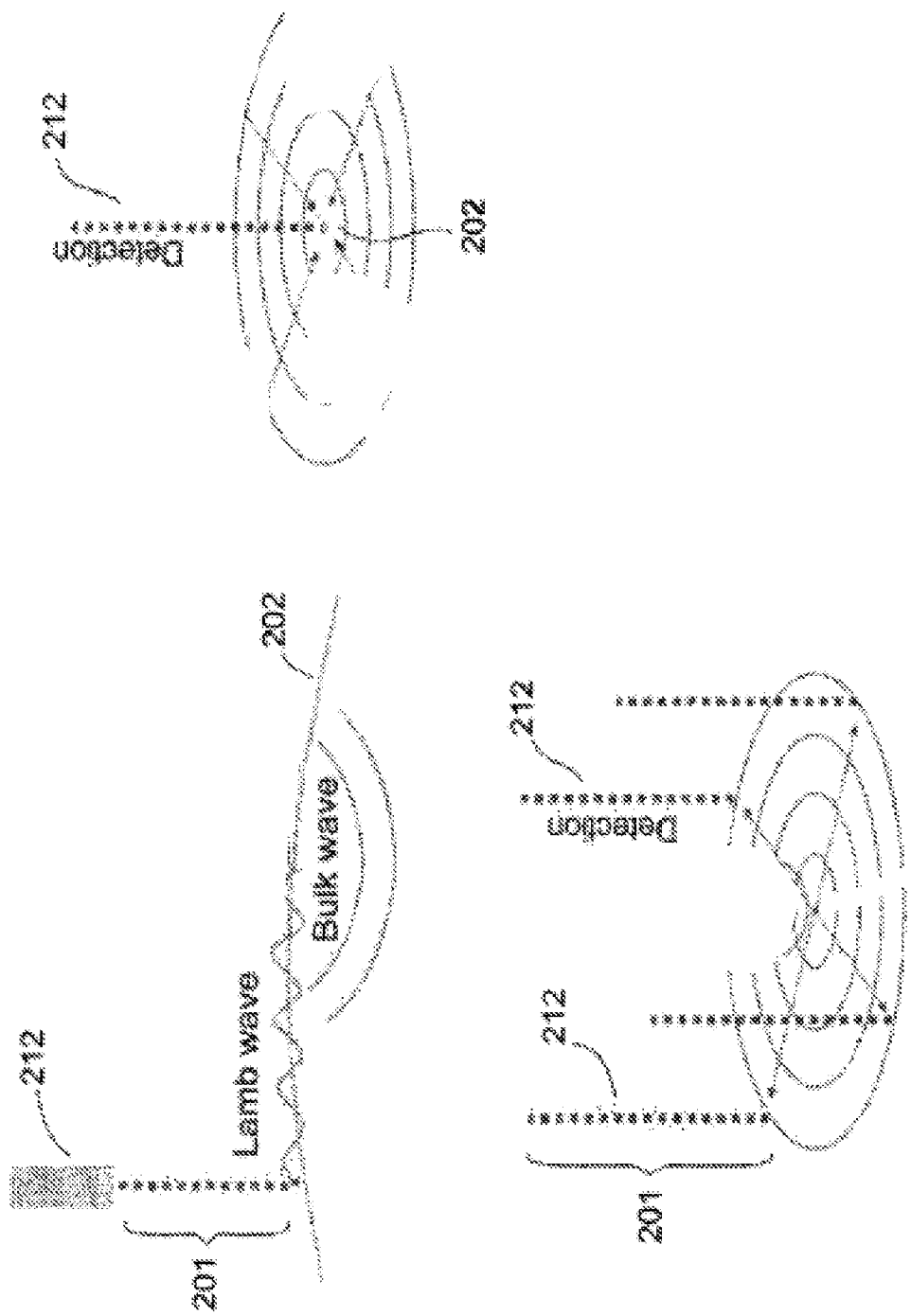
FIG. 1 presents a first exemplary embodiment according to the present disclosure.

A contactless, fast and advanced device and method are disclosed to measure IOP without need for anaesthetics. An IOP reading that is both precise (i.e., unbiased) and features small uncertainty in the IOP estimate can be realized. This is achieved by an IOP measurement arrangement for measuring the pressure in an eye of a patient. The arrangement can include at least one source for producing mechanical waves of several frequencies from a distance to the eye of the patient to generate at least one surface wave to the eye, means for detecting at least one surface wave from a distance from the eye to extract surface wave information, and means to determine pressure information of the eye based on said surface wave information.

An intraocular pressure measurement method is disclosed for measuring pressure in an eye of a patient. The method produces mechanical waves of several frequencies from a distance to the eye of the patient to generate at least one surface wave to the eye, detects at least one surface wave from a distance from the eye to extract surface wave information, and determines pressure information of the eye based on said surface wave information.

Mechanical waves of several frequencies can be sent from a distance through air to the eye of the patient to generate at least one surface wave to the eye. At least one surface wave from a distance from the eye can be detected to form surface wave information for determination of pressure information of the eye.

Exemplary embodiments enable patient and user friendly use with no need to touch sensitive surfaces of an eye, together with advanced methods to process measurement information in order to extract qualified pressure information of the eye. One benefit is that exemplary embodiments can be utilized from one patient to another with less risk for contamination as contact to the eye is avoided.

Essentially, excitation and/or detection of electromagnetic waves can be performed by means of a beam of electromagnetic waves produced for example, by a laser, pulsed laser or a plasma source (focused laser or a spark gap), which is for example mediated via an electromagnetic waveguide (e.g., an optical fiber, collimator, lenses, masks and/or an arrangement of mirrors) and targeted onto the eye of a patient or onto a spot in the vicinity of the patient's eye. An input of the electromagnetic wave into or onto the eye is followed by electromagnetic-mechanical conversion (e.g., photo-acoustic conversion) that generates little heat and significant mechanical vibration into the eye's tissues or a plasma source that launches sound waves that impinge on the eye to create a wave in it. Correspondingly, mechanical vibrations of the eye tissue are detected (e.g., by means performing optical interferometry, optical coherence tomography, laser Doppler vibrometry or by an ultrasound transducer). Exemplary embodiments can generate a mechanical wave or waves (e.g. ultrasonic waves) in the eye and detect the waves in the eye. The potential applications relate especially to determination of IOP; i.e., an eye pressure.

In exemplary embodiments non-contacting photoacoustic and ultrasonic intraocular pressure (IOP) measurement techniques can include the following exemplary requirements: non-contact excitation and detection methods, which are safe for the patient, determination of essentially accurate intraocular pressure (IOP) values, possibility to provide follow-up of patient's IOP values, and these techniques can be used by a health care professional and/or by a patient in a convenient and ergonomic way with lowered risk for contamination from patient to patient.

There are several physical interactions that could be exploited for the IOP measurement. These interactions will be explained in order to evaluate their usability for a non-contact ultrasonic IOP measurement:

A) Physical systems such as the eye may vibrate at certain resonance frequencies when they are mechanically or photo-acoustically disturbed. These frequencies depend on the mechanical properties of the components of the eye, and on the IOP as well as on eye size and shape as well as properties of the eye socket. Measurement of the resonance frequencies can be rather easy to implement, and preliminary data can be utilized to support the viability of the resonance measurements. Guided waves, such as Lamb waves or quasi-Lamb waves or membrane waves that propagate on curved structures can also be used in the measurements.

B) Lamb waves are guided waves that travel along a structure. They are dispersive; i.e., the phase velocity of a Lamb wave depends on the frequency of the wave. Thus, with a single broadband excitation one can measure the dispersion relation of the waves, which is closely related to both the elasticity of the structure and stress caused by external pressure such as for example the IOP. Broadband dispersion measurements provide more accurate IOP estimates than narrow band measurements. Several independent measurements can be performed on different parts of the eye, which can increase accuracy and decrease the confounding effect of the elasticity of for example, the cornea of the eye as well as the effect of the eye socket. Preliminary data support the viability of the proposed method. Localized testing along lines can be performed, which could allow spatial averaging and could provide localized data as well as anisotropy data.

C) Bulk wave velocities; i.e., longitudinal and shear ultrasonic wave velocities, probe mechanical properties of measured materials. The propagation velocity of the longitudinal wave depends on the static pressure loading the material (e.g. liquid) in which it propagates, and the phenomena can be utilized to determine for example, IOP. Bulk waves are simple to generate and measure, but for accurate (e.g., IOP) measurements, other measurements than bulk wave measurements are needed, because bulk wave measurements itself are unlikely to achieve high accuracy.

D) Ultrasonic waves, both Lamb and bulk waves, loose energy as a function of propagation distance. This energy loss decreases as a function of pressure for bulk waves, but in loaded plates (e.g., the eye) due to the loading on the surface by the IOP, the effect is reversed. Quantitative measurements can be performed to calibrate the effects of external pressure on Lamb wave attenuation. Attenuation analysis is likely to be useful when combined with other properties (e.g., speed of sound, dispersion).

FIG. 1 presents a first exemplary embodiment according to the present disclosure, in which a spark gap 210 is placed near but not in contact with the sclera of the eye 202. The spark generates a wave that upon contacting the sclera launches two kinds of vibrations: first, elastic waves (Lamb $S_0$ and $A_0$ guided ultrasonic modes), followed by a resonant vibration of the sclera and the cornea. The vibration can be picked up with a custom made one-point interferometer 212 capable of detecting the time-of-arrival of the wave. The mode map (i.e., frequency-velocity chart of Lamb waves traveling along the sclera) depends on the intra-ocular pressure (IOP). Also resonant frequencies depend on IOP. This kind of embodiment is affordable and simple to produce and allows adding detectors to increase the measurement accuracy. Also a high signal-to-noise ratio can be achieved by this kind of implementation.

The spark gap 210 produces a bright flash of light that might harm the eye 202. This can be avoided with a thin black membrane not in contact with the eye. The membrane passes the acoustic pressure wave and blocks the light from reaching the eye. The weak mechanical nonlinear wave generated by the spark can be audible and does not induce tissue-breaking stress. The intensity of the emitted wave can be controlled to ensure that there is no risk to the hearing. Also the detectors can use very low power lasers (even Class 1) in order to introduce no safety risks to the eye.

The first exemplary embodiment can be improved by incorporating a custom made one-point interferometer capable of measuring vibration as a function of time. This increases costs, but allows simultaneous measurement of both the resonance and the traveling Lamb waves, thus yielding more accurate IOP measurement information.

Figure 2:
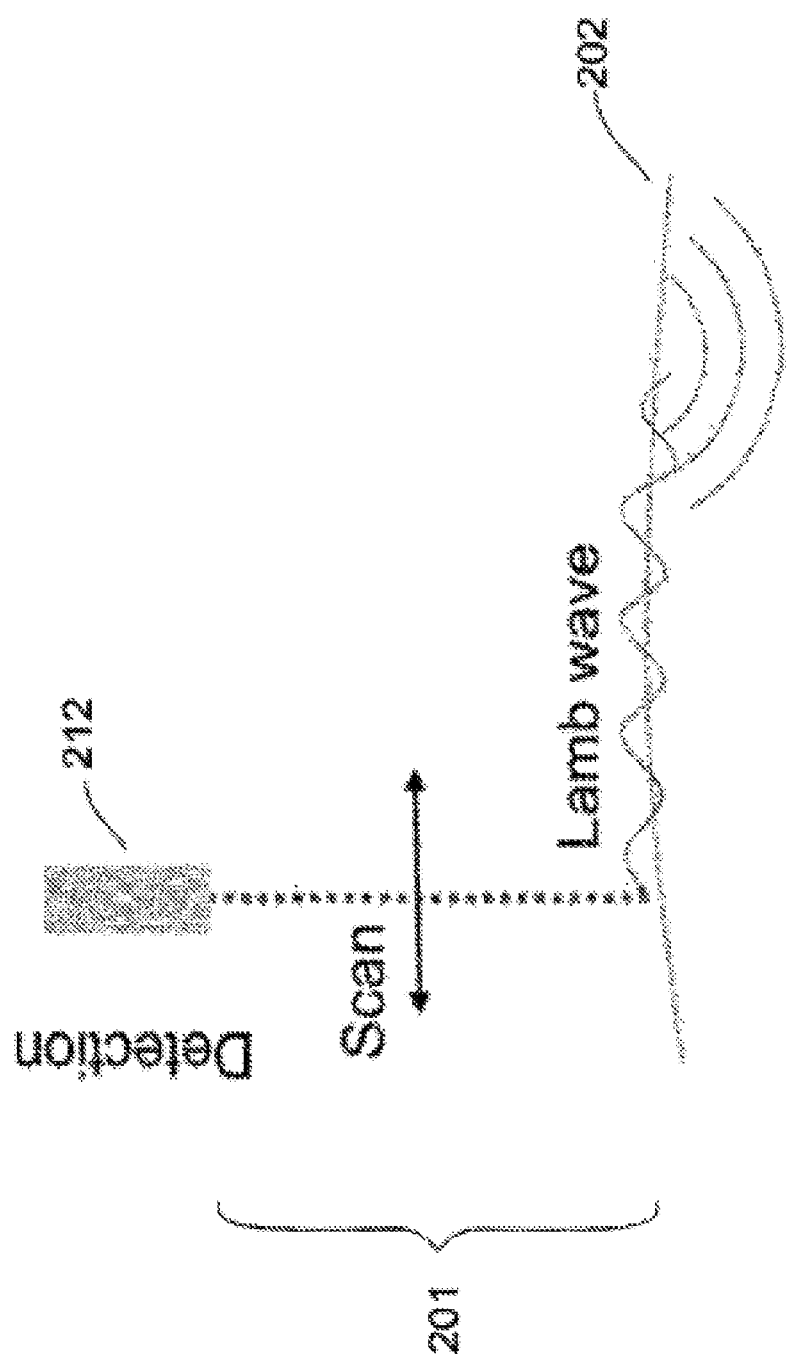
FIG. 2 presents second exemplary embodiment according to the present disclosure.

FIG. 2 presents a second exemplary embodiment according to the present disclosure, in which a pulsed (e.g., KrF excimer) laser 210 (e.g. 248 nm) is used to excite mechanical wave(s) with a detection (e.g., a laser Doppler vibrometer (LDV) as detecting means 212). The excimer laser can be focused on either the sclera or the cornea of the eye 202 or close to them both, launching Lamb waves to the eye which are detected by a detection system 212 (e.g., the LDV). Several parameters can concurrently be detected and correlated and calibrated to IOP: speed of sound, attenuation, vibration spectrum of the received signal, detected resonance frequency, etc.

UV wavelengths (or 1300-1550 nm IR (infrared)) absorb strongly into the cornea, and are thus unlikely to traverse the sclera. Interferometers use generally a Class 1 beam, which is safe to the eye. The generated Lamb waves do not cause discomfort or damage. For example, the 248 nm wavelength absorbs extremely well into both the cornea and the sclera, thus not damaging eye structures beneath them. Benefits of such an embodiment are also low intensity values which causes no discomfort to the patient and high absorption coefficient which improves signal to noise ratio and hence both precision and accuracy of the IOP estimate. Also phase-delayed laser diodes can be used to shape the spectrum of the transmit signal to increase the signal to noise ratio in the four modes in the mode map that is analyzed.

In first and second exemplary embodiments according to the present disclosure photoacoustic IOP measurements based on Lamb wave velocity dispersion and resonant frequencies of the eye/sclera are accomplished. A bi-modality embodiment (i.e. concurrent use of Lamb wave measurements and resonance measurements) can be accomplished for example, by four detection points to pick up the wave excited in the middle to allow four simultaneous and independent measurements. This provides precision. The sensor 212 can also include ultrasonic transducers coupled to air which to serve as distance and tilt measurement devices. An IOP measurement device (e.g. FIG. 3) according to the present disclosure can, for example, include a spark gap 210 in the middle of the device, detection means to pick up the excited waves from four points around an excitation point on the surface of the eye 210 and a built-in ultrasonic sensor 220 detecting the distance of the device from the eye and the tilt of the device. The device can include direction lights or a display unit to indicate into which direction it should be tilted. This makes it more operator friendly.

Figure 3:
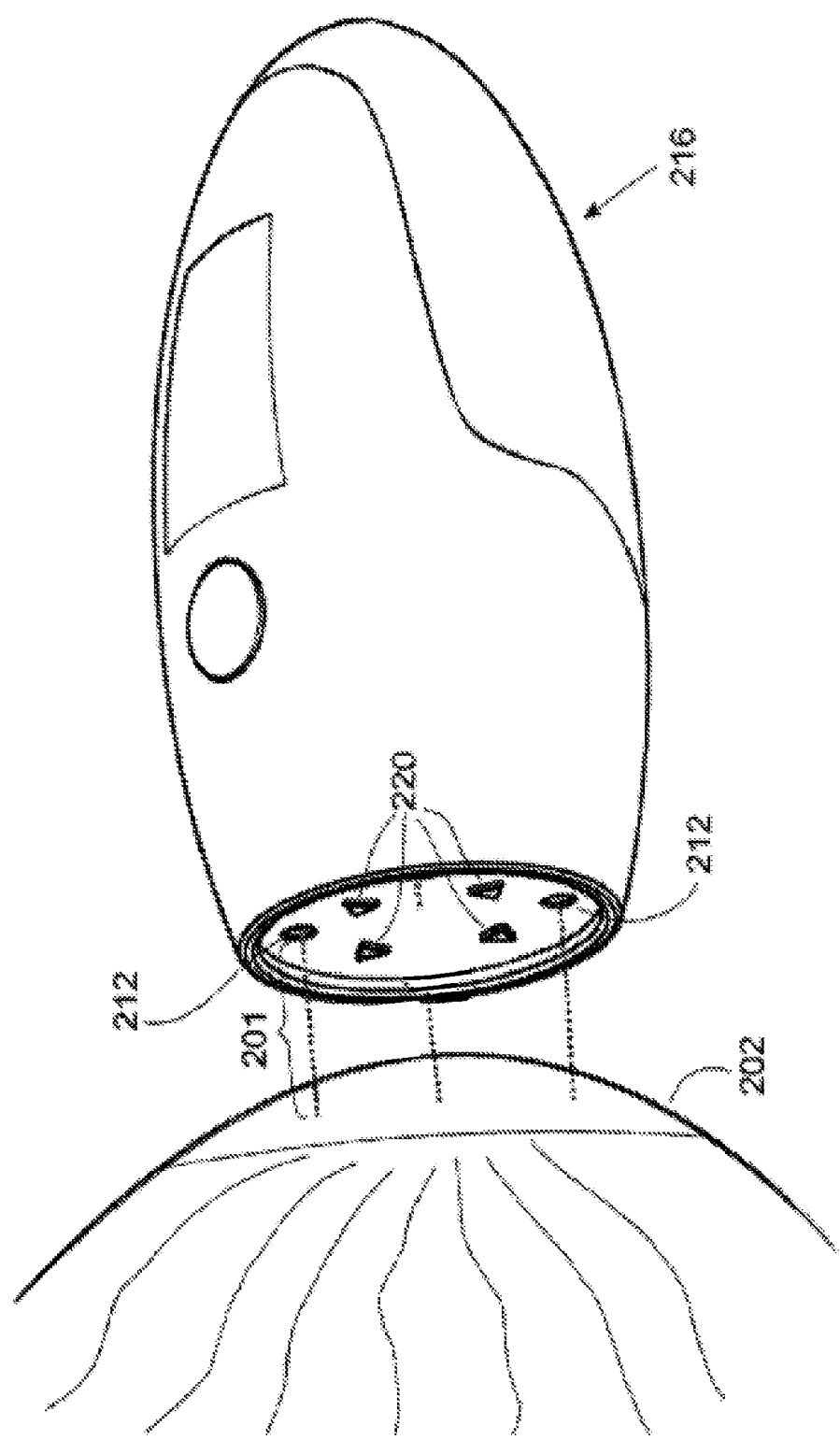
FIG. 3 presents another exemplary embodiment according to the present disclosure.

FIG. 3 presents a first exemplary intraocular pressure (IOP) measurement arrangement according to the present disclosure for measuring the pressure in an eye 202 of a patient. The arrangement includes at least one source 210 for producing mechanical waves of several frequencies from a distance 200 through air to the eye 202 of the patient. The waves generate at least one surface wave to the eye, and more specifically to a certain surface area of the eye and near the surface area of the eye. The embodiment can enable probing a certain site of the eye if one wants to and even a certain direction along the eye ball. The surface waves can include modes (e.g., Lamb $S_0$ and $A_0$ guided ultrasonic modes), and also resonant vibrations that are generated to the eye. The source 210 is for example, a spark gap 210 that generates by at least one spark an acoustic nonlinear wave (e.g., shock wave) that couples to the eye 202 through the air and generates for example, both Lamb waves and resonant vibrations to the surface of the eye 202 and into the eye 202. The surface wave or waves are detected by means 212 for detecting from a distance 201 from the eye 202 to form surface wave information. Resonant vibrations can be detected by means 212 for detecting from a distance 201 from the eye 202 to form resonance information. Detection of the propagating Lamb waves can for example, be based on the time-of-arrival of the first arriving signal (FAS), whereas the detection of the resonances can for example, be based on the Fourier transform of the measured signal.

As will be apparent to those skilled in the art, the mechanical nonlinear wave can also be generated by a mechanical impact of a combination of two hard surfaces or corners or edges (210) as the source (210) for producing nonlinear acoustic or mechanical waves, such as shock waves, of several frequencies from a distance (200) the waves coupling to the eye (202) of the patient. For example, it is known that a hammer strike can produce nonlinear wide spectrum acoustic signal including ultrasonic frequencies.

The distance 200 or the distance 201, or both of them, can be optimized by means 220 for controlling distance. The means 220 can be implemented for example by ultrasonic transducers coupled to air for distance or tilt measurements and aiding the operator to position the device. Also accelerometers or gyroscopes can be used to detect the best position and time moment for the measurements. The means 220 for controlling and setting an optimized distance 200, 201 from the source 210 and from the means 212 to the surface of the eye 202 can also be implemented by an embodiment, in which the means 220 includes at least one laser emitting visible light, and at least two (e.g., light) guides having first ends and second ends, the first ends connected to the laser for receiving visible light. The means 220 can also include positioning means for moving the source 210 for producing mechanical waves or the detecting means 212 into different points (e.g. along a predetermined path). Each of the second ends provides a light beam, and these light beams are directed towards a surface of the eye 202 with an angle of convergence K. The light beams are adjusted to intersect in a predetermined focus point, which is visible on the surface of the eye and which indicates the proper position and distance 200, 201 from the source 210 and from the means 212 to the surface of the eye 202.

The arrangement in FIG. 3 also includes means 216 for determining pressure information of the eye based on the surface wave information and for example based also on the resonance information. The means 216 can be implemented by for example a processor unit in an IOP measurement device or by a separate computer unit to which measurement information is sent from the IOP measurement unit via a wireless or wired connection link. The means 212 for detecting can be implemented for example by means of optical interferometry (i.e., by an optical interferometer), by means of optical coherence tomography (i.e., by an optical coherence tomography device), or by means of laser Doppler vibrometry (i.e. by a laser Doppler vibrometer), or by ultrasonic measurements using at least one ultrasonic transducer, or with a combination of the different techniques. In a first exemplary arrangement the means 212 for detecting at least one surface wave includes at least one interferometer 212, which can measure the vibrations as a function of time, and which allows simultaneous measurement of both the resonance vibrations and of the surface waves (i.e., the Lamb waves), thus yielding a precise and accurate estimate of the pressure of the eye 202. Exemplary embodiments can use one inexpensive single point interferometer or more of them to detect time of arrival.

There can be either at least two wave sources 210 or detecting means 212, or at least two of both, to improve measurement accuracy in forming the surface wave information and the resonance information. In an exemplary arrangement of FIG. 3 the detecting means 212 are in three different detection locations in order to improve measurement accuracy and precision and to obtain higher signal-to-noise ratio.

Heartbeat, eye blinking, and respiration cause temporal fluctuations in intraocular pressure. Of these, the heartbeat causes relatively constant pulsatile peaks in IOP, normally between 2-3 mmHg. This difference is called ocular pulse amplitude. This amplitude depends on heart rate and axial length and there is a positive linear correlation between ocular pulse amplitude and IOP. High IOP causes high ocular pulse amplitude. Several other parameters, including ocular rigidity affects the magnitude of the ocular pulse amplitude. These pressure peaks cause vibrations and waves along the eyeball (sclera and cornea) and also internally (e.g., iris), and the waves and vibrations can be detected (e.g. optically). An exemplary device according to the present disclosure can be used to measure, monitor, and analyze these heart beat induced changes in the vibrations and waves to estimate IOP also without external stimulus.

Embodiments according to the present disclosure can improve comfort, accuracy, and precision of the IOP measurement by utilizing at least one of the following features: 1) employing non-contacting measurement (comfort), 2) employing a localized and directional measurement (reduces eye shape-induced bias (error) to improve accuracy), 3) employing a slow wave form (symmetric & asymmetric Lamb waves, which reduces the confidence limits of the sound velocity estimate=improves the precision of the elasticity estimate=improves the precision of the IOP estimate, 4) employing a broadband signal which allows mapping several propagating modes to gain precision in the sound velocity estimate (improves precision and potentially accuracy of the tester) 5) employing a geometric transmit and receive array or phased array (improved SNR which reduces the confidence limits of the sound velocity estimate due to larger signals and due to ability to fit the estimate with a regression line, this improves precision), 6) the array approach also allows tuning the modes to be employed for improved SNR and consequently precision and accuracy of the tester/test, 7) employing both the travelling wave approach described above and the known resonance concept. Since these measurements are independent of each other a more sensitive and robust tester follows (it should improve both precision and accuracy). The measurement can be generalized to other physical parameters such as sound attenuation (absorption, scattering) and sound velocity dispersion.

In an exemplary embodiment according to the present disclosure, patient heartbeat or breathing or both of them is used as a source for producing surface waves of several frequencies detectable by means 212 from a distance 201 to the eye 202 of the patient. In another embodiment according to the present disclosure, means 210 to generate tiny plasma burst is used as the source 210 for producing acoustic waves of several frequencies from a distance 200 to the eye 202 of the patient. The generation can be made by sparking or by focusing a laser ray to one point on the surface of the eye or close to the surface of the eye. In an exemplary embodiment according to the present disclosure, means 210 to generate chemical reaction is used as the source 210 for producing acoustic waves of several frequencies from a distance 200 to the eye 202 of the patient.

In further exemplary embodiments according to the present disclosure, mode tuning is used by phase delayed excitation in source 210 for producing mechanical waves of several frequencies from a distance 200 through air to the eye 202 of the patient. An improved signal to noise ratio (SNR) and improved time of flight (TOF) estimate can be achieved by mode tuning performed on the basis of phase delayed excitation. Precision and accuracy of TOP measurements according to the present disclosure can thus be increased.

Also, in exemplary embodiment according to the present disclosure, a photoacoustic laser-based excitation can be performed by having a ring shaped form to the surface of the eye or close to that surface in order to amplify the surface wave in the middle of the ring shape. This enables easier and more accurate detection to be performed by the detection means. It also permits a cheaper receiver to be used. The user can combine the use of a shaped (i.e., circle or line or crescent) source with the phased array concept having many dots, lines or crescents for improved precision and accuracy in the IOP measurement.

On the basis of the present disclosure an ideal tonometer can be implemented which is capable of measuring intraocular pressure with fast comfortable measurements without anesthetic and disposable waste, and of operation by an unskilled operator.

Although the invention has been presented in reference to the attached figures and specification, the invention is not so limited. It will be appreciated by those skilled in the art that be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

The invention claimed is:

1. An intraocular pressure measurement arrangement for measuring pressure of an eye of a patient, wherein the eye includes a sclera and a cornea, the intraocular pressure measurement arrangement comprising:
    a contactless wave detector that is locatable at a detection distance from the eye,
    the wave detector being configured to detect at least one surface wave produced on the eye by at least one of a patient heartbeat or breathing and containing plural wave components having frequencies corresponding to at least one of patient heartbeat frequencies and patient breathing frequencies, the at least one surface wave being produced without stimulus provided by the intraocular pressure measurement arrangement,
    the wave detector being configured to detect a part of the at least one surface wave that contains the wave components having the at least one of patient heart-beat frequencies and patient breathing frequencies, and
    wherein the intraocular pressure measurement arrangement does not comprise any source for producing acoustic or mechanical waves from a distance to the eye of the patient to generate the at least one surface wave to the eye such that the wave detector is configured to detect the part of the at least one surface wave from a surface of the eye when the eye is open,
    the detected part of the at least one surface wave that contains the wave components having the at least one of patient heartbeat frequencies and patient breathing frequencies and containing surface wave information dependent on the ocular pressure of the eye; and
    an intraocular pressure measurement unit comprising a processor operatively connected to an output of the wave detector to receive the surface wave information, the intraocular pressure measurement unit for determining pressure of the eye based on said surface wave information dependent on the ocular pressure of the eye and providing the determined pressure of the eye as an output of the intraocular pressure measurement arrangement.

2. An intraocular pressure measurement arrangement according to claim 1, wherein the wave detector comprises at least one interferometer configured to measure vibrations as a function of time for the surface wave that contains the wave components having the at least one of patient heartbeat frequencies and patient breathing frequencies.

3. An intraocular pressure measurement arrangement according to claim 1, wherein the wave detector is configured to detect the part of the at least one surface wave that contains the wave components having the at least one of patient heartbeat frequencies and patient breathing frequencies at least in two different detection locations in order to improve measurement accuracy and to obtain higher signal-to-noise ratio.

4. An intraocular pressure measurement arrangement according to claim 1, wherein the wave detector comprises an optical interferometer configured to detect and measure said wave components resulting from heartbeat and/or respiration and containing ocular pulse amplitude information correlated to the intraocular pressure (TOP).

* * * * *